United States Patent [19]

Geen et al.

[11] Patent Number: 5,138,057
[45] Date of Patent: Aug. 11, 1992

[54] CHEMICAL PROCESS FOR THE PREPARATION OF PURINE DERIVATIVES

[75] Inventors: Graham R. Geen, Epsom; John C. Hanson, Betchworth, both of England

[73] Assignee: Beecham Group p.l.c., Brentford, England

[21] Appl. No.: 409,526

[22] Filed: Sep. 19, 1989

[30] Foreign Application Priority Data

Sep. 21, 1988 [GB] United Kingdom ............... 8822236

[51] Int. Cl.$^5$ .................. C07D 473/40; C07D 473/26
[52] U.S. Cl. .................................... 544/277; 544/276
[58] Field of Search ........................... 544/277, 276

[56] References Cited

U.S. PATENT DOCUMENTS

| | | | |
|---|---|---|---|
| 4,347,185 | 8/1982 | Muchowski et al. | 548/516 |
| 4,347,187 | 8/1982 | Muchowski et al. | 548/453 |
| 4,798,833 | 1/1989 | Johansson et al. | 514/262 |
| 5,017,701 | 5/1991 | Grinter et al. | 544/277 |
| 5,066,805 | 11/1991 | Kincey | 544/277 |

FOREIGN PATENT DOCUMENTS

| | | | |
|---|---|---|---|
| 0182024 | 5/1986 | European Pat. Off. | 544/277 |
| 0203685 | 12/1986 | European Pat. Off. | 544/277 |
| 0302644 | 2/1989 | European Pat. Off. | |
| WO87/05664 | 9/1987 | PCT Int'l Appl. | 544/277 |

OTHER PUBLICATIONS

Padgett, et al., J. Org. Chem., vol. 44, No. 20, pp. 3492-3496 (1979).
Csendes, et al., J. Org. Chem., vol. 44, No. 23, pp. 4173-4178 (1979).
Gerster, et al., Chemical Abstracts, vol. 689: 87494q (1968).
Robins, et al., Chemical Abstracts, vol. 84: 150914z (1976).
Boswell, et al., Chemical Abstracts, vol. 92: 76855c (1980).

*Primary Examiner*—Diana G. Rivers
*Attorney, Agent, or Firm*—Hopgood, Calimafde, Kalil, Blaustein & Judlowe

[57] ABSTRACT

A process for the preparation of a compound of formula (I)

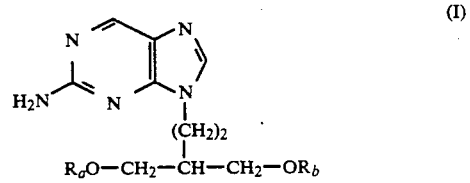

which process comprises reacting a compound of formula (II):

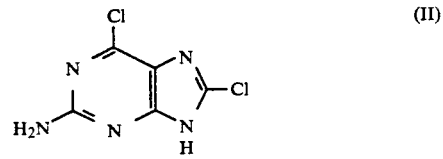

wherein the amino group is optionally protected, with a side chain intermediate of formula (III):

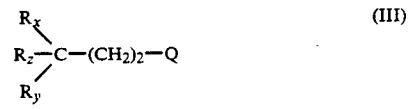

wherein Q is a leaving group, $R_x$ and $R_y$ are protected hydroxymethyl or acyloxymethyl, or group(s) convertible to hydroxymethyl or acyloxymethyl; and $R_z$ is hydrogen or a group convertible thereto; and thereafter converting the 6- and 8- chloro substituents to hydrogen by means of reduction; converting $R_x$ and $R_y$ when other than hydroxymethyl or acyloxymethyl, to hydroxymethyl or acyloxymethyl, optionally converting $R_x/R_y$ hydroxymethyl to acyloxymethyl or vice versa, deprotecting the 2-amino group where necessary and converting $R_z$, (when other than hydrogen) to hydrogen; and optionally forming a pharmaceutically acceptable salt thereof.

6 Claims, No Drawings

CHEMICAL PROCESS FOR THE PREPARATION OF PURINE DERIVATIVES

The present invention relates to a novel chemical process for the preparation of purine derivatives which have antiviral activity.

EP-A-182024 (Beecham Group p.l.c.) describes compounds of formula (I):

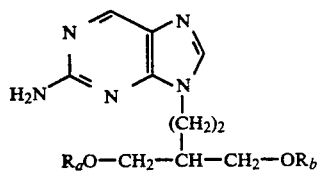

wherein $R_a$ and $R_b$ are independently hydrogen or a group RCO—wherein R is phenyl or $C_{1-18}$ alkyl.

The compound of formula (B) within formula (I):

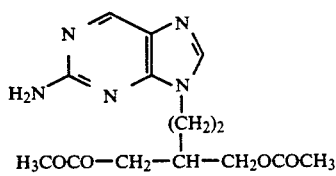

is of particular interest as an antiviral agent (BRL 42810 or famciclovir).

The process already described for the preparation of the compounds of formula (I) involves the reaction of a purine intermediate, 2-amino-6-chloropurine of formula (C):

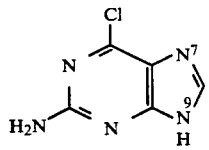

with a side chain intermediate of formula (D):

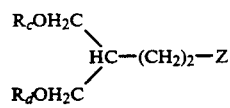

wherein $R_c$ and $R_d$ are independently acyl groups or hydroxy protecting groups and Z is a leaving group, such as halo, for example chloro, bromo, iodo; and thereafter converting the 6-chloro group to hydrogen by reduction methods.

The intermediate of formula (C) is prepared by chlorination of guanine, as described in EP-A-203685 (Beecham Group p.l.c.). Despite this improvement in the method of production of 2-amino-6-chloropurine, the isolable yield at this chlorination step is sufficiently low that there is a need for alternative routes to compounds of formula (I).

It has surprisingly been discovered that, by introducing an 8-chloro substituent into the compound of formula (C), the yield of corresponding purine intermediate is increased, and therefore increasing the overall yield of the resulting compound of formula (I).

Accordingly, the present invention provides a process for the preparation of a compound of formula (I), or a pharmaceutically acceptable salt thereof, which process comprises reacting a purine intermediate of formula (II):

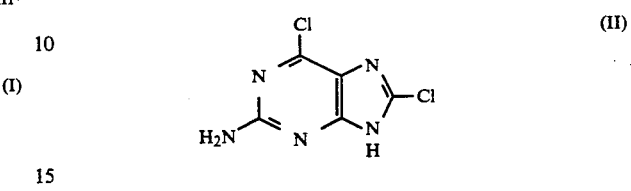

wherein the amino group is optionally protected, with a side chain intermediate of formula (III):

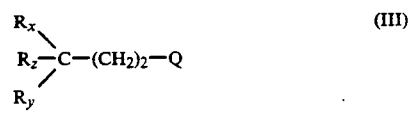

wherein Q is a leaving group, $R_x$ and $R_y$ are protected hydroxymethyl or acyloxymethyl, or group(s) convertible to hydroxymethyl or acyloxymethyl; and $R_z$ is hydrogen or a group convertible thereto; and thereafter converting the 6- and 8- chloro substituents to hydrogen by means of reduction; converting $R_x$ and $R_y$ when other than hydroxymethyl or acyloxymethyl, to hydroxymethyl or acyloxymethyl, optionally converting $R_x/R_y$ hydroxymethyl to acyloxymethyl or vice versa, deprotecting the 2-amino group where necessary and converting $R_z$, (when other than hydrogen) to hydrogen; and optionally forming a pharmaceutically acceptable salt thereof.

The intermediates formed in this reaction are of formula (IV):

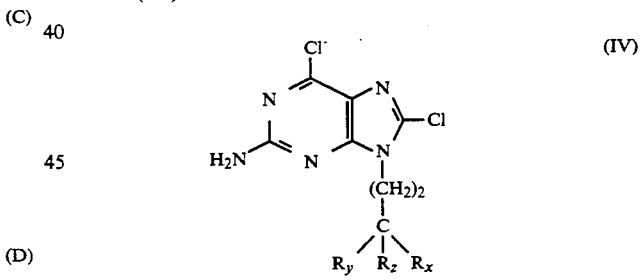

which are novel and form an aspect of the invention.

The reaction may be carried out in an inert solvent, for example dimethylformamide, dimethylsulphoxide or acetonitrile, preferably dimethylformamide, in the presence of an inorganic or organic base, over a temperature range from 0° C. to the boiling point of the solvent, usually 30–40° C. Examples of inorganic bases include alkali metal hydrides, alkali metal carbonates such as sodium or potassium carbonate and preferably potassium carbonate. Suitable organic bases are 1,8-diazabicyclo[5.4.0]undec-7-ene and tetramethyl guanidine.

Suitable examples of the leaving group Q, include halo, such as chloro, bromo or iodo, and tosyloxy and mesyloxy.

Suitable examples of hydroxy protecting groups (other than acyl groups) include the t-Butyl dimethylsilyl group removable by 80% acetic acid at elevated temperatures, around 90° C., or by treatment with tetrabutyl ammonium fluoride in a solvent, such as tetrahydrofuran, at ambient temperature.

Another suitable protecting group is wherein the two hydroxy groups in formula (III) (when $R_x$ is hydroxymethyl) are reacted with 2,2-dimethoxypropane, forming a 1,3-dioxan ring. This group may be removed by acidic hydrolysis.

Other suitable protecting groups include substituted benzyl groups such as p-methoxybenzyl, removable by treatment with 2,3-dichloro-5,6-dicyanobenzoquinone.

Other suitable protecting groups are apparent to those skilled in the art.

$R_x$ and/or $R_y$ may be acyloxymethyl, such as a group $RCO_2CH_2$ wherein R is as defined in formula (I). Examples of R include methyl, ethyl, n- and iso-propyl, n- and iso-, sec- and tert-butyl, preferably methyl.

Interconversion of $R_x/R_y$ acyloxymethyl and hydroxymethyl may be carried out conventionally as described in EP-A-141927.

Other suitable values of $R_x$, $R_y$, $R_z$ include wherein the compounds of formula (III) is of formula (IIIA) or (IIIB)

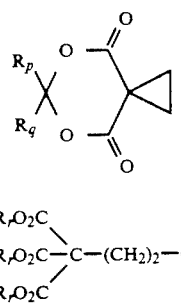

(IIIA)

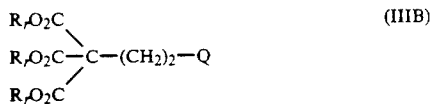

(IIIB)

wherein $R_p$ and $R_q$ are independently hydrogen, $C_{1-4}$ alkyl or phenyl, or $R_p$ and $R_q$ together are $C_{4-6}$ polymethylene; and $R_r$ is $C_{1-6}$ alkyl or phenyl $C_{1-6}$ alkyl, in which any phenyl moieties are optionally substituted. Optional substituents include one or two groups selected from $C_{1-4}$ alkyl, halo and $C_{1-4}$ alkoxy. Halo includes iodo, bromo, chloro and fluoro; alkoxy/alkyl includes those containing methyl, ethyl, n- and iso-propyl.

When the compound of formula (IIIA) is used, the resulting intermediate is of formula (IVA):

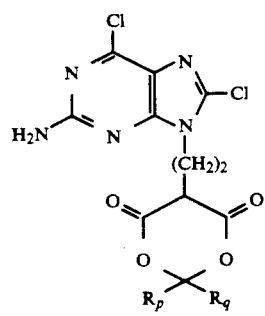

(IVA)

when the compound of formula (IIIB) is used, the resulting intermediate is of formula (IVB):

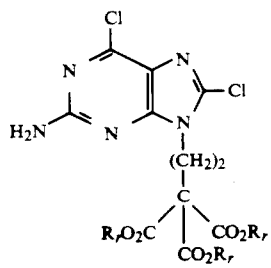

(IVB)

Values for alkyl groups $R_p$ and $R_q$ and $R_r$ include these values listed as suitable for R in formula (I), preferably methyl for $R_p$ and $R_q$ and ethyl for $R_r$. In on $R_p$ and $R_q$ may together be $C_4$ or $C_5$ polymethylene.

The intermediates of formulae (IVA) and (IVB) are subsequently converted to an intermediate of formula (V):

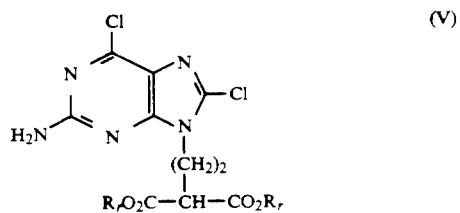

(V)

by transesterification and hydrolysis/decarboxylation respectively by methods analogous to those disclosed in EP-A-0302644.

An intermediate of formula (V) is convertible to a compound of formula (VI):

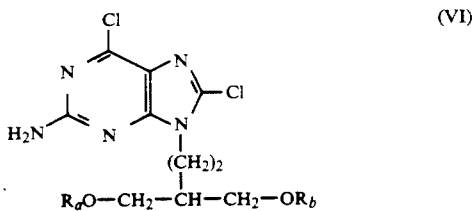

(VI)

by reduction, under conventional conditions using, for example, sodium borohydride.

It is preferred, however, that the intermediate of formula (III) is of formula (III)':

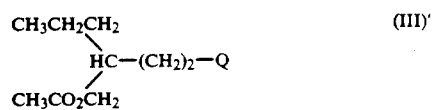

(III)' for the preparation of compounds of formula (A) and (B) as defined, because:

i) Compounds of formula (III)' give a particularly good N9:N7 ratio (regioselectivity).

ii) Ease of separation of N9:N7 isomers.

The 2-amino group may be protected, for example, using a benzyl protecting group, removable by hydrogenolysis. It may also be protected by an acyl group, for example acetyl, removable by hydrolysis.

The conversion of the chloro substituents to hydrogen by means of reduction takes place conventionally, according to the methods described for reduction of the 6-chloro substituent in EP-A-182024.

Pharmaceutically acceptable salts are formed conventionally.

The purine intermediate of formula (II) is novel and forms an aspect of the present invention.

It may be prepared by chlorination of guanine by:

i) reacting guanine with a sulphur oxychloride in the presence of chloride ions, to give 8-chloroguanine of formula (VII):

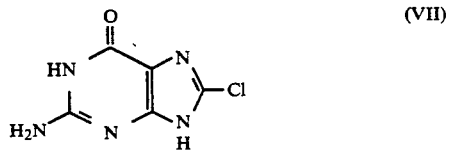
(VII)

Suitable sulphur oxychlorides include $SOCl_2, SO_2Cl_2$, $MeSO_3Cl$ and $TsCl$. Suitable sources of chloride ions include quaternary ammonium chlorides such as tetraalkyl substituted ammonium chlorides, for example $Et_4NCl$, $Et_3MeNCl$, $Et_2Me_2NCl$, EtMe piperidinium chloride and $Et_2NPh$. HCl. The reaction takes place at elevated temperatures 30°–100° C. preferably 50°–80° C. in a solvent such as acetonitrile, dichloromethane, chloroform or methanesulphonic acid. Alternatively, the chlorinating agent may also function as the solvent.

ii) reacting 8-chloroguanine with phosphorus oxychloride in the presence of chloride ions, in analogous manner to the chlorination of guanine itself, described in EP-A-203685, which corresponds to U.S. Pat. No. 4,736,029, incorporated herein by reference.

It will be appreciated that steps i) and ii) may be carried out in reverse order, via 2-amino-6-chloropurine, although this route is less preferred.

Intermediates of formula (III) wherein $R_x/R_y$ are protected hydroxymethyl or acyloxymethyl may be prepared as described in EP-A-141927 and EP-A-182024 (both Beecham Group p.l.c), or by analogous methods thereto.

Intermediates of the formula (IIIA) are known or are prepared by analogous methods, such as that described in Organic Syntheses Vol 60, page 66.

Intermediates of formula (IIIB) are known or prepared by analogous methods. The compound of formula (IIIB) wherein Q is bromo and $R_r$ is ethyl may be prepared from triethyl methanetricarboxylate according to the procedure described by H. Rapoport et.al., J. Org. Chem., 44, 3492(1979).

It will also be appreciated that the side chain intermediate of formula (III) may be replaced by an appropriate side chain for the preparation of other 6-deoxy guanine antiviral agents, such as those described in EP-A-108285 (The Wellcome Foundation Limited), which corresponds to U.S. Pat. Nos. 4,544,634, 4,609,662, 4,649,140, 4,695,570, and 4,745,119, all incorporated herein by reference, and EP-A-186640 (Astra Läkemedel Aktiebolag).

The following Examples illustrate the invention.

DESCRIPTION 1

Precaration of 2-amino-8-chloro-6-hydroxypurine (8-chloroquanine)and its hydrochloride salt

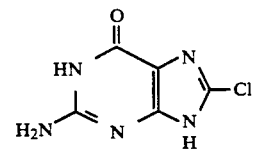

Method 1

A mixture of guanine (22.5 g), methyltriethylammonium chloride (88 g) and thionyl chloride (50 ml) was slowly heated and stirred at 50°–70° C. for ½h, then kept at 70° C. for a further ½h. The reaction mixture was then cooled and the excess thionyl chloride removed under vacuum. The residue was poured into water and the pH adjusted to 7 to give a tan-coloured precipitate. In order to expedite filtration and to achieve further purification, the pH was further adjusted to 13 with 40% sodium hydroxide solution, any insoluble material filtered off, and the resulting solution acidified slowly to pH 8 allowing the product to crystallize, particularly at pH 11.5. The solid was filtered, washed with acetone and air dried at 40° C. to give the title compound as a buff solid (28.5 g) (water assay 14.1%). Vacuum drying at 40° C. afforded a solid analysing as a monohydrate.

I.R. 3380, 3200, 3100, 1670 $cm^{-1}$.

M.S. (negative ion F.A.B.) 184, 186 (M-H).

Found: C, 29.33; H, 2.62; N, 34.59%. $C_5H_4N_5OCl.H_2O$;

requires: C, 29.50; H, 2.97; N, 34.40%.

Method 2

Sulphuryl chloride (3.3 ml) was added to a stirred mixture of guanine (3.02 g) and methyltriethylammonium chloride (13 g) in acetonitrile (22 ml). The reaction temperature increased slowly to 50° C., and was maintained at 50° C. for a further 45 minutes by heating, The mixture was then cooled, poured into water and the pH adjusted to 7. The crude product was isolated by filtration or purified as in Method 1.

Method 3

Guanine (1.52 g) was dissolved with warming in a mixture of methane sulphonic acid (10 ml), thionyl chloride (10 ml), and tetraethylammonium chloride (6 g). The mixture was heated to 80° C. for 1 h, cooled and poured into water. The product was isolated as in Method 1. (Thionyl chloride may be replaced by phosphorus oxychloride or methanesulphonyl chloride).

HCl salt 8-chloroguanine (2 g), dissolved in hot water (40 ml) and concentrated hydrochloric acid (25 ml), was treated with charcoal, filtered and the filtrate cooled to 4° C. overnight to give the title compound as an off-white solid (1.2 g) analysing as a monohydrate.

Found: C, 24.73; H, 3.25; N, 29.36, Cl, 28.95%. $C_5H_4N_5OCl$. HCl. $H_2O$.

requires: C, 25.02; H, 2.94; N, 29.18; Cl 29.54%.

$^{13}C$ n.m.r. ($D^6$-DMSO) 112.0, 135.6, 149.4, 152.7, 152.9 p.p.m.

Description 2

Preparation of 2-Amino-6,8-dichloropurine

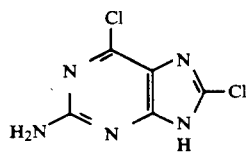

Method 1

8-chloroguanine (vacuum dried at 115° C. over phosphorus pentoxide) (2.04 g) was added to a solution of methyl triethylammonium chloride (6.6 g) in acetonitrile (11 ml). Phosphorus oxychloride (5.6 ml) was then added and the mixture heated to 60° C. for 1 h. The mixture was then cooled, and the solvent and excess phosphorus oxychloride removed under vacuum. Water was added, the pH adjusted to 3 and the mixture stirred overnight at room temperature to complete hydrolysis of the phosphorus containing intermediates. The pH was then adjusted to 10, the solution treated with charcoal, filtered and acidified slowly to pH 5. The fine crystals were filtered off, washed with acetone and air dried at 40° C., giving the title compound as an off-white solid (1.78 g), analysing as a hemihydrate (water assay 4.1%).

I.R. 3330, 3190, 1680, 1630, 1570 cm$^{-1}$.

M.S. (electron impact) 203, 205, 207 M$^+$(Cl$_2$ isotope pattern); 168, 170 (M$^+$—Cl).

$^{13}$C n.m.r. (D$^6$-DMSO) 122.9, 138.6, 147.4, 155.9, 159.8 p.p.m.

Found: C, 28.29; H, 1.92; N, 33.27%. C$_5$H$_3$N$_5$Cl$_2$.½H$_2$O.

requires: C, 28.19; H, 1.89; N, 32.88%.

U.V. (EtOH) $\lambda_{max}$ 219, 246, 311 nm.

Method 2

2-Amino-6-chloropurine (3.4 g) was added to a solution of methyl triethyl ammonium chloride (13 g) in acetonitrile (22 ml). Sulphuryl chloride (5 ml) was added and the reaction mixture heated to 60° C. for 24 h, cooled, poured into water (150 ml) and the pH adjusted to 9 with 40% sodium hydroxide solution. Charcoal was then added, the mixture filtered and the filtrate acidified slowly to pH 4.5 to give the title compound as a solid which was filtered off (3.9 g).

EXAMPLE 9-(4-Acetoxy-3-acetoxymethylbut-1-yl)-2-aminocurine (BRL 42810)

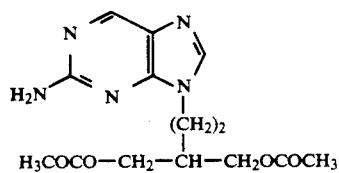

Method 1

(a) 2-Acetoxymethyl-4-iodobutyl-1-acetate (9.4 g) was added to a stirred mixture of 2-amino-6,8-dichloropurine (5.8 g) and anhydrous potassium carbonate (5.9 g) in N,N-dimethylformamide (100 ml), and the resulting mixture stirred at ambient temperature overnight. The reaction mixture was filtered and the filtrate evaporated to give a thick gum which was shown by $^1$H n.m.r. analysis to be a mixture of the N-9 and N-7 alkylated purines in the ratio 17:1 respectively. T.l.c. (5% methanol-dichloromethane) showed two products of rf=0.24, 0.32; corresponding to the N-7 and N-9 alkylated purines. Column chromatography on silica (eluant 2.5% methanol-dichloromethane) of the gum afforded 9-(4-acetoxy-3-acetoxymethylbut-1-yl)-2-amino-6,8- dichloropurine, which was crystallised from ethyl acetate-diethyl ether to give a colourless solid (4.7 g) m.p. 118°-119° C.

$^1$H n.m.r (D$^6$-DMSO)δ6 1.83 (q, 2H, >CHCH$_2$CH$_2$—), 2.03 (s, 6H, —CH$_3$), 2.05 (m, 1H, >CH—), 4.07 (m, 4H, —CH$_2$O—), 4.15 (t, 2H, >NCH$_2$—), 7.05 (brs, 2H, -NH$_2$).

Found: C, 43.13; H, 4.48; N, 18.07%. C$_{14}$H$_{17}$N$_5$O$_4$Cl$_2$ requires: C, 43.09; H, 4.39, N, 17.95%.

(b) A mixture of 9-(4-acetoxy-3-acetoxymethylbut1-yl)-2-amino-6,8-dichloropurine (3.9 g), 5% palladium on charcoal (0.5 g) and triethylamine (3.1 ml) was suspended in ethanol (250 ml) and hydrogenated at 50 p.s.i. overnight. The reaction was initially heated to 60° C., and then allowed to cool to ambient temperature The reaction mixture was filtered and the filtrate evaporated. The residue was taken up in water (100 ml) and extracted with dichloromethane (2×200 ml). The organic extracts were combined and dried over magnesium sulphate. Filtration and evaporation gave the title compound as a gum which crystallized on standing. Recrystallization from butan-1-ol gave a colourless solid (2.4 g) m.p. 102°-103° C.

$^1$H n.m.r. (D$^6$-DMSO)δ1.88 (m, 3H, >CHCH$_2$CH$_2$—), 2.00 (s,6H, —CH$_3$), 4.03 (d, 4H, —CH$_2$O—), 4.14 (t, 2H, >NCH$_2$—), 6.45 (brs, 2H, —NH$_2$), 8.09 (s, 1H, H-8), 8.57 (s, 1H, H-6).

Method 2

A mixture of 2-amino-6,8-dichloropurine (2.04 g), 6,6-dimethyl-5,7-dioxaspiro[2.5]octane-4,8-dione (1.73 g) and anhydrous potassium carbonate (2.12 g) in N,N-dimethylformamide (40 ml) was stirred at room temperature for 18 hours under dry nitrogen. The solvent was evaporated and the residue dissolved in water (60 ml) and acidified from pH 10 to pH 4 with dilute hydrochloric acid. The yellow precipitate was filtered off, washed with water and dried to give 2-amino-6,8-dichloro-9-[1-(2,2-dimethyl-1,3-dioxane4,6-dione-5-yl)eth-2-yl]purine (2.2 g, 50%). T.l.c. r.f. 0.65 (25% methanol-dichloromethane).

$^1$H n.m.r.(D$^6$-DMSO)δ1.69 (s,3H,CH$_3$), 1.79(S,3H,CH$_3$), 2.42(m,2H,CHCH$_2$), 4.31(t,2H, NCH$_2$), 4.4(vbr s, 2H, NH$_2$+H$_2$O), 4.56(t,1H,CHCH$_2$).

BRL 42810 is prepared from the above compound by methods analogous to those disclosed in EP-A-302644:
i) Reduction (see Description 12)
ii) Trans-esterification (see Example 2)
iii) Reduction (see Method d))
iv) Acetylation (see Method c))

Method 3

A mixture of 2-amino-6,8-dichloropurine (0.82 g), 5-bromoethyl-2,2-dimethyl-1,3-dioxan (0.9 g) and anhydrous potassium carbonate (0.83 g) in N,N-dimethylformamide (20 ml) was stirred at room temperature for 18 hours under dry nitrogen. The mixture was then filtered and the filtrate evaporated. The residue was purified by column chromatography on silica (100 g) [eluent 2% methanol-dichloromethane] to give 2-amino-6,8-dichloro-9-(2-(2,2-dimethyl-1,3-dioxan-5-yl)ethyl)purine (t.l.c. r.f. 0.50, 5% methanol-dichloromethane) as a pale solid (0.62 g, 45%). Recrystallisation from diethyl ether gave an off-white solid m.p. 149°-150° C.

$^1$H n.m.r. (D$^6$-DMSO):δ1.28(s,3H,CH$_3$), 1.33(s,3H,CH$_3$), 1.62(m,1H,CHCH$_2$), 1.70(m,2H,CH$_2$CH$_2$CH), 3.56(dd,2H,2xH$_{AX}$), 3.84(dd,2H,2xH$_{EQ}$), 4.06(t,2H, NCHHD 2), 7.06(br s,2H,NH$_2$).

Elemental analysis: Found: C: 45.01, H: 4.89, N:20.25; C$_{13}$H$_{17}$N$_5$O$_2$Cl$_2$ requires; C: 45.10, H: 4.95, N:20.23.

BRL 42810 is prepared from the above compound by methods analogous to those disclosed in EP-A-302644:
i) Reduction (see Description 12)
ii) Hydrolysis (see Method e))
iii) Acetylation (see Method c))

Method 4

Ethyl 4-bromo-2,2-dicarboethoxybutanoate (8.2 g) was added to a stirred mixture of 2-amino-6,8-dichloropurine (4.08 g) and anhydrous potassium carbonate (4.14 g) in N,N-dimethylformamide (80 cm$^3$) and the resulting mixture stirred at 70°-80° C for 72 hours under dry nitrogen. The reaction mixture was cooled to room temperature, filtered and the filtrate evaporated. T.l.c. [3% methanol-dichloromethane] showed one major spot r.f.=0.44. The residue was purified by column chromatography on silica (200 g) [eluent=2% methanol-dichloromethane]to give 2-amino-6,8-dichloro-9-(ethyl-2,2-dicarboethoxybutanoate -4yl) purine (2.6 g 28%) as a yellow solid. Recrystallization from ethyl acetate/diethyl ether gave an off-white solid m.p. 153°-155° C.

$^1$H n.m.r. (D$^6$-DMSO)δ1.22(t,9H,—CH$_2$CHHD 3), 2.50(t,2H,—CH$_2$C ), 4.23(q,6H,—CH$_2$CH$_3$), 4.31(t,2H, N—CHHD 2), 7.02 (br s,2H,NH$_2$).

Elemental analysis: Found; C: 44.35, H: 4.57, N: 15.09;
C$_{17}$H$_{21}$N$_5$O$_6$Cl$_2$ requires; C: 44.17, H: 4.58, N: 15.15.

BRL 42810 is prepared from the above compound by methods analogous to those disclosed in EP-A-302644:
i) Reduction (see Description 12)
ii) Decarbethexylation (see Example 3)
iii) Reduction (see Method b))
iv) Acylation (see Method c))

We claim:
1. A process for the preparation of a compound of formula (I):

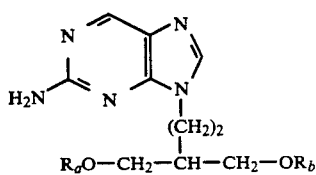

wherein R$_a$ and R$_b$ are independently hydrogen or a group RCO— wherein R is phenyl or C$_{1-18}$ alkyl, which process comprises reacting a compound of formula (II):

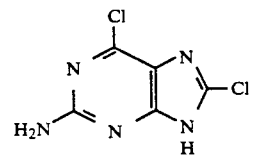

wherein the amino group is optionally protected, with a side chain intermediate selected from formulae (IIIA), (IIIB), and (III)':

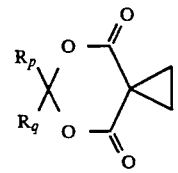

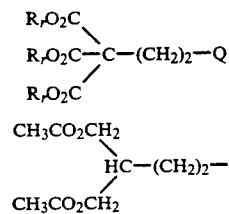

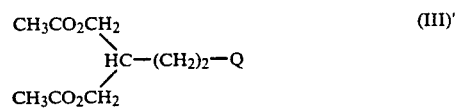

wherein R$_p$ and R$_q$ are independently hydrogen, C$_{1-6}$ alkyl or phenyl, or R$_p$ and R$_q$ together are C$_{4-6}$ polymethylene, R$_r$ is C$_{1-6}$ alkyl or phenyl C$_{1-6}$ alkyl in which the phenyl optionally has substituted thereon one or two groups selected from halo, C$_{1-4}$ alkyl, and C$_{1-4}$ alkoxy, and Q is a leaving group; and thereafter converting the 6- and 8- chloro substituents to hydrogen by means of reduction; converting R$_p$ and R$_q$, or two of the three R$_r$ moieties in formula (IIIB), when other than hydroxymethyl or acyloxymethyl, to hydroxymethyl or acyloxymethyl, optionally converting hydroxymethyl to acyloxymethyl or vice versa, deprotecting the 2-amino group where necessary, and converting the third of said three R$_r$ moieties (when other than hydrogen) to hydrogen; and optionally forming a pharmaceutically acceptable salt thereof.

2. A process as defined in claim 1, wherein Q is fluoro, chloro, bromo, iodo, tosyloxy or mesyloxy.

3. A process according to claim 1, for the preparation of the compound of formula (I), wherein R$_a$ R$_b$ are each —COCH$_3$.

4. A compound of formula (IV)

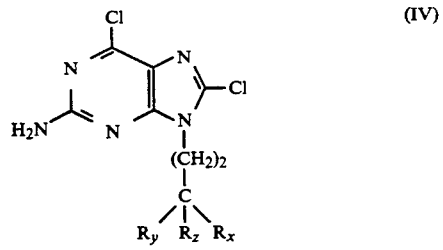

wherein R$_x$ and R$_y$ are protected hydroxymethyl or acyloxymethyl or group(s) convertible to hydroxymethyl or acyloxymethyl, and R$_z$ is hydrogen or a group convertible thereto.

5. A compound selected from the group consisting of:
9-(4-Acetoxy-3-acetoxymethylbutyl-1-yl)-2-amino-6,8-dichloropurine,
2-Amino-6,8-dichloro-9-purine,
2-Amino-6,8-dichloro-9(2-(2,2-dimethyl-1,3-dioxan-5-yl)ethyl)purine, or
2-Amino-6,8-dichloro-9-(ethyl-2,2-dicarboethoxybutanoate-4-yl)purine.

6. 2-Amino-6,8-dichloropurine.

* * * * *

UNITED STATES PATENT AND TRADEMARK OFFICE
CERTIFICATE OF CORRECTION

PATENT NO. : 5,138,057
DATED : August 11, 1992
INVENTOR(S) : Graham R. Geen, et. al.

It is certified that error appears in the above-indentified patent and that said Letters Patent is hereby corrected as shown below:

On the Title page, item [75], after "Geen" replace "Epsom" with -- Harlow--, and after "Hanson" replace "Betchworth" with --Epsom--.

Item [56], on the Title page, under "FOREIGN PATENT DOCUMENTS" change "W087/056604" to --W087/05604--, and under "OTHER PUBLICATIONS", after "Gerster, et. al." change "vol. 689" to --vol. 68--.

Col. 11, line 64, change "2-Amino-6,8-dichloro-9-purine" to —2-Amino-6,8-dichloro-9-[1-(2,2-dimethyl-1,3-dioxane-4,6-dione-5-yl)eth-2-yl]purine—.

Signed and Sealed this

Seventh Day of September, 1993

Attest:

BRUCE LEHMAN

*Attesting Officer*   Commissioner of Patents and Trademarks